(12) United States Patent
Herscovici-Cohen et al.

(10) Patent No.: US 9,770,190 B2
(45) Date of Patent: Sep. 26, 2017

(54) METHOD AND APPARATUS FOR EXAMINING SUBJECTS FOR PARTICULAR PHYSIOLOGICAL CONDITIONS UTILIZING ACOUSTIC INFORMATION

(75) Inventors: Sarah Herscovici-Cohen, Zikhron-Yaakov (IL); Robert P. Schnall, Kiryat-Bialik (IL)

(73) Assignee: Itamar Medical Ltd., Caesarea (IL)

( * ) Notice: Subject to any disclaimer, the term of this patent is extended or adjusted under 35 U.S.C. 154(b) by 42 days.

(21) Appl. No.: 12/994,865

(22) PCT Filed: May 26, 2009

(86) PCT No.: PCT/IL2009/000528
§ 371 (c)(1),
(2), (4) Date: Nov. 29, 2010

(87) PCT Pub. No.: WO2009/144721
PCT Pub. Date: Dec. 3, 2009

(65) Prior Publication Data
US 2011/0092857 A1    Apr. 21, 2011

Related U.S. Application Data

(60) Provisional application No. 61/071,992, filed on May 29, 2008.

(51) Int. Cl.
*A61B 7/00*  (2006.01)
*A61B 5/08*  (2006.01)
*A61B 5/00*  (2006.01)

(52) U.S. Cl.
CPC ............... *A61B 5/08* (2013.01); *A61B 7/003* (2013.01); *A61B 5/4806* (2013.01); *A61B 2560/0223* (2013.01)

(58) Field of Classification Search
CPC ....... A61B 5/08; A61B 5/4806; A61B 5/4818; A61B 5/4821; A61B 7/003
(Continued)

(56) References Cited

U.S. PATENT DOCUMENTS 4,784,162 A   11/1988 Ricks et al.
5,797,852 A    8/1998 Karakasoglu et al.
(Continued)

FOREIGN PATENT DOCUMENTS

WO   WO 2009/144721   12/2009

OTHER PUBLICATIONS

International Preliminary Report on Patentability dated Dec. 9, 2010 From the International Bureau of WIPO Re. Application No. PCT/IL2009/000528.
(Continued)

*Primary Examiner* — Rene Towa
*Assistant Examiner* — May Abouelela (57) ABSTRACT

A method and apparatus for examining a subject for a particular physiological condition according to a technique which utilizes sounds generated by the subject and sensed at a predefined distance from the site of sound generation of the subject, by locating a first sound sensor, e.g., a sound level meter which measures the sound levels in decibels, on a particular region of the subject's body to produce an output corresponding to the sound level sensed thereby; modifying the output of the first sound level meter by a pre-calculated Transfer Function equating its output to that of a second sound level meter located at a predefined distance from the site of sound generation of the subject's body; and utilizing the modified output of the first sound level meter in determining the existence of the particular physiological condition.

21 Claims, 4 Drawing Sheets

(58) Field of Classification Search
USPC .......................................................... 600/586
See application file for complete search history.

(56) References Cited

U.S. PATENT DOCUMENTS

| | | | |
|---|---|---|---|
| 5,853,005 | A | 12/1998 | Scanlon |
| 6,213,955 | B1 | 4/2001 | Karakasoglu et al. |
| 2003/0100843 | A1 | 5/2003 | Hoffman |
| 2004/0039295 | A1 | 2/2004 | Olbrich et al. |
| 2006/0037615 | A1 | 2/2006 | Wilkinson et al. |
| 2006/0064037 | A1 | 3/2006 | Shalon et al. |
| 2006/0155205 | A1* | 7/2006 | Sotos et al. ................. 600/529 |

OTHER PUBLICATIONS

International Search Report and the Written Opinion dated Sep. 15, 2009 From the International Searching Authority Re.: Application No. PCT/IL09/00528.
Translation of Office Action dated Nov. 28, 2012 From the State Intellectual Property Office of the People's Republic of China Re. Application No. 200980130922.1.
Translation of Search Report dated Nov. 28, 2012 From the State Intellectual Property Office of the People's Republic of China Re. Application No. 200980130922.1.
Supplementary European Search Report and the European Search Opinion dated Aug. 23, 2013 From the European Patent Office Re. Application No. 09754340.9.
Translation of Notice of Reason for Rejection dated Aug. 6, 2013 From the Japanese Patent Office Re. Application No. 2011-511161.
Translation of Office Action dated Aug. 7, 2013 From the State Intellectual Property Office of the People's Republic of China Re. Application No. 200980130922.1.
Office Action dated Nov. 28, 2012 From the State Intellectual Property Office of the People's Republic of China Re. Application No. 200980130922.1 and Its Translation Into English.
Search Report dated Nov. 28, 2012 From the State Intellectual Property Office of the People's Republic of China Re. Application No. 200980130922.1 and Its Translation Into English.
Notice of Reason for Rejection dated May 2, 2014 From the Japanese Patent Office Re. Application No. 2011-511161 and Its Translation into English.
Request for Examination dated Mar. 28, 2013 From the Federal Service of Intellectual Property, Federal State Budget Institute, Federal Institute of Industrial Property of the Russian Federation Re. Application No. 2010153388 and Its Translation Into English.
Communication Pursuant to Article 94(3) EPC dated Jun. 25, 2014 From the European Patent Office Re. Application No. 09754340.9.
Requisition by the Examiner dated Aug. 25, 2015 From the Canadian Intellectual Property Office Re. Application No. 2,725,320.
Communication Pursuant to Article 94(3) EPC dated Feb. 17, 2016 From the European Patent Office Re. Application No. 09754340.9.
Requisition by the Examiner dated Apr. 22, 2016 From the Canadian Intellectual Property Office Re. Application No. 2,725,320.
Examination Report Under Sections 12 & 13 of the Patents Act, 1970 and the Patents Rules, 2003 dated May 23, 2017 From the Government of India, Patent Office, Intellectual Property Office Re. Application No. 2654/MUMNP/2010. (7 Pages).

\* cited by examiner

METHOD AND APPARATUS FOR EXAMINING SUBJECTS FOR PARTICULAR PHYSIOLOGICAL CONDITIONS UTILIZING ACOUSTIC INFORMATION

RELATED APPLICATIONS

This Application is a National Phase of PCT Patent Application No. PCT/IL2009/000528 having International filing date of May 26, 2009, which claims the benefit of U.S. Provisional Application No. 61/071,992 filed on May 29, 2008. The contents of the above Applications are all incorporated herein by reference.

FIELD AND BACKGROUND OF THE INVENTION

The present invention relates to methods and apparatus for examining subjects for particular physiological conditions using acoustic information. The invention is particularly useful in known techniques which utilize sounds generated by the subject and sensed at a predefined distance from the site of sound generation of the subject's body, e.g., one meter, and is therefore described below with respect to such techniques.

The measurement of the acoustic characteristics of certain body functions, particularly those related to breathing, or cessation of breathing, or partial cessation of breathing provides valuable medical information. Cases in point include, but are not limited to, the measurement of snoring intensity, which is an important medical parameter particularly in the domain of sleep medicine. Other examples related to the respiratory system include the intensity of wheezing, stridor, (high-pitched sounds), coughing, respiratory rates, etc., which are clinically important in diagnosing various respiratory system conditions. In addition, sounds related to the cardiovascular system, such a the well known 'heart sounds', sounds related to the musculo-skeletal system, sounds related to the gastro-intestinal system, and sounds related to specific measurement methods, such as blood pressure measurements, are also clinically important.

Measurement of the intensity of snoring is important in providing an index of the state of a patient's respiratory activity and the state of the airways during sleep. It is affected by, among other physiological factors, the degree of patency of a patient's airways, the upper airway muscle tone, mucosal swelling, and the degree of respiratory drive particularly during sleep. Measurement of the frequency spectrum of snoring sounds may also provide useful clinical information, for example, in determining the main site of the snores origin in the subject's respiratory system.

Quantitative calibration of such acoustic activity is essential for enabling the medical practitioner to gage the clinical significance of, for example, a subject's snoring activity, as a part of the diagnostic process. Traditionally, the intensity of snoring sounds has been determined as the decibel level of such sounds at some predefined distance, commonly one meter from the site of sound generation. Established clinical criteria for quantifying snoring intensity are defined in this manner.

In clinical laboratory based medicine, and in particular in the sleep medicine clinic setting, the recording of a subject's acoustic activity is traditionally performed by placing a sound level recorder, such as a microphone, at a predefined distance (e.g., one meter) from the subject. The setting up of such an acoustic measurement environment calls for considerable technical expertise and is thus clearly not suitable for performing measurements outside the confines of specialized laboratories. It is also highly susceptible to environmental acoustic activity, such as other snoring bed partners, audio devices etc., which may seriously confound the accurate measurement of a given subject's breathing activity.

In practice, measurements outside the specialist laboratory are being increasingly applied. In particular, these include ambulatory measurement systems which assume an important role in clinical medicine, and are particularly valuable in sleep medicine. The advantages of ambulatory testing are numerous and well known, and include increased patient comfort, accessibility, as well as considerable cost saving.

A major advantage, among others, in recording respiratory sound activity directly from the subject's body surface is that it considerably reduces the problem of acoustic crosstalk due to environmental noise activity, which problem is inherent to sound level measurement at a fixed distance from the subject.

The acoustic quality associated with various physiological systems may also be influenced by the movement of the body at the examination site, and also the position, posture or orientation, with respect to gravity, of the body at the examination site. Moreover, diagnosing many physiological conditions utilize not only acoustic information, but also such position and/or motion information.

The determination of multiple physiological signals, including body position, body movement and acoustic measurements related to physiological processes of the body, have been involved in a number of patent publications, including U.S. Pat. Nos. 4,784,162, 5,275,159, 6,171,258 and U.S. Patent Application 2005/0113646 A1. In these prior patent applications the measurements of body position, body movement and/or acoustic activity, was generally achieved by using separate sensors on the body surface. These sensors were not designed to enable measurement from a single common location, nor were they configured to permit them to be arranged in such a way as to facilitate measurement from a single location.

Other patent publications relative to this field are U.S. Pat. Nos. 6,468,234, 7,077,810, and International PCT Application of International Publication No. WO2005/120167. However, the developments described therein do not use acoustical or sound sensors, but rather vibration sensors sensing vibrations of the subject's body.

There are several reasons why obtaining information concerning the body position, body movement and acoustic measurements from a common site wherein the means for obtaining this information are housed within a common housing is beneficial to the assessment of a variety of physiological and pathological conditions, as illustrated by the following examples:

Application for Respiratory System

The occurrence of upper-airway increased resistance, or even complete collapse, is a hallmark of the well known obstructive sleep apnea (OSA) syndrome. An obstructive event in a patient with OSA is usually preceded by considerable acoustic activity or snoring, however this ceases when the flow of air is sufficiently attenuated due to the progression of airway narrowing.

The disappearance of snoring may, on the other hand, merely be due to a reversal of the partial airway obstruction which caused the snoring. Distinguishing between these two extreme situations may be facilitated by measuring surface motion at the measurement site. In the case of the worsening obstruction, increased surface motion which is sub-acoustic in nature is likely to be present by ongoing vibration of the tissues due to large pressure perturbations at the site of obstruction brought about by ineffectual breathing effort. An appropriate motion sensor will enable this to be sensed.

Although there are a number of locations on the body surface that may be appropriate for recording acoustic, and/or vibratory activity associated with snoring and sleep disordered breathing conditions, we have found that the best site for such measurements is the extra thoracic region extending from the chin to the sternum, and the thoracic region surrounding the supra-sternal notch. At these sites the sound and surface motion signals are best recorded due to close proximity to the source of the perturbations, and due to there being mainly soft tissues between the body surface and the airway lumen.

In order to effectively measure these multiple parameters from this region, it is highly desirable to obtain the full set of body position, body movement and acoustic information measurements from a single location. The present invention specifically addresses this objective.

Application for Blood Pressure Measurements

There are a number of well known methods for performing non-invasive blood pressure measurements. Two of the most common are the so called "Auscultatory" method and the "oscillometric" method, respectively.

In the ausculatory method, acoustic information detected by stethoscope, associated with varying degrees of arterial opening during the progressive deflation of the blood pressure cuff, are sensed, and according to the quality of the associated sound, the respective systolic and diastolic pressure values may be determined. This is the most commonly used method in clinical practice, and the so "Korotkoff" sounds are used to define the blood pressure values. Automatic devices which analyze the acoustic information are also available.

The second commonly used blood pressure measurement method is the so called "oscillometric" method, which is based on detecting fluctuations in the volume of the measured limb segment associated with varying degrees of arterial opening during the progressive deflation of the blood pressure cuff. According to the amplitude of the associated volume changes, the respective systolic, mean and derived diastolic pressure values may be determined. Sensing of the volume change is usually based on pressure change in the cuff or the magnitude of the skin motion in the vicinity of the measured artery.

In both of the above methods, the inventive device of the current application would have distinct advantages over either method alone since it would be able to provide the source information needed for the determination of BP according to both methods.

Furthermore, the addition of a body position detecting means in, for example, the traditional measurement of BP from brachial artery of the arm, would provide important information regarding the orientation of the measurement site, which could for instance be used to determine the hydrostatic offset of the arm in a seated patient, based on the angle of the arm with respect to the long axis of the body.

Finally, in the above application, accurate positioning of the sensor is critical to the success of the measurement since the location of the pulsating area is highly limited. Only an apparatus having all the sensors located at the exact site would provide sufficiently reliable data.

Cardiology

The application of both acoustic and surface motion sensing, as well as body position determination from a single common site, wherein the means for obtaining this information are housed within a common housing, may provide useful information about heart function, as illustrated in the following example.

The detection of heart sounds is a commonly used clinical practice which is particularly helpful in, among other things, detecting valvular heart disease conditions.

The clinical interpretation of the significance of the heart sounds may be affected by a patient's breathing. For example, in the so called second heart sound (which, is caused by reverberations within the blood and surrounding tissues associated with the sudden blocking of retrograde blood flow due to closure of the aortic valve and pulmonary valve respectively at the end of ventricular systole), knowledge of the patient's breathing can enable a diagnosis to be made by helping to determine if the "splitting" of the heart sound is pathological or physiological in nature.

In essence, this is related to the effect of intra-thoracic pressure on blood return into the right side of the heart. During inspiration, greater negative intra-thoracic pressure is generated which increases the blood volume in the right ventricle. This prolongs the time that the pulmonary valve stays open relative to the aortic valve.

This situation thus results in a physiological "splitting" of the second heart sound.

If however, this splitting does not vary with inspiration, it may represent a pathological state, possibly due to a left-to-right shunt of blood within the heart itself. This raises the concern of an atrial or ventricular septal defect.

Certain clinical interventions can be performed to increase the venous return to the right side of the heart, including the adoption of a supine posture, which can enhance the above described diagnosis.

In the above described example, a combined body position, body movement, and acoustic measurements apparatus would be very useful since it would facilitate the accurate recording of the heart sounds via the acoustic sensing means, the breathing pattern via the combination of body position and body movement signals, and the patients posture by the body position sensor, when it is appropriately placed on the patient's chest wall.

In addition, vibrations related to the mechanical perturbations associated with heart valve closure, and pathological conditions thereof, which are sub-acoustic in nature, may be present at the signal measurement site. An appropriate motion sensor will enable this to be sensed.

As was the case in the previously cited examples, here too, accurate positioning of the sensor is critical to the success of the measurement since the location at which heart sounds, and particularly splitting of the second heart sound area, is highly limited. Only an apparatus having all the sensors located at the exact site would provide sufficiently reliable data.

Rheumatology

The combined body position, body movement, and acoustic measurements apparatus may also be useful for quantitatively detecting and analyzing joint disorders by measuring joint movements related to sound patterns.

Since the apparatus can be used to provide a limb's position in 3D space over time, and can be used to characterize the dynamics the limb movements, the associated sound information may therefore provide a quantitative assessment of the degree of joint damage. As was the case in the previously cited examples, here too, accurate positioning of the sensor is critical to the success of the measurement. Clearly, given the limited space available for placing the apparatus at the joint location, only an apparatus having all the sensors located at the exact site would enable the measurements to be properly made to provide sufficiently reliable data.

Gastroenterology

The evaluation of several physiological processes related to the gastrointestinal system may be beneficially performed by using a combined body position, body movement, and acoustic measurements apparatus and the appropriate signal analysis. Such processes as swallowing (deglutition), peristalsis, bowel sounds, bowel transit time, may be thus analyzed. Furthermore, the use of multiple units may be beneficially applied at appropriate body sites to facilitate the evaluation. For example, applying multiple units on the surface of the abdomen overlying the intestines may be useful in determining the bowel transit time and the kinetics of bowel action and its disorders. Likewise, when applied to the throat/neck and thorax regions such units may be useful in evaluating swallowing and related disorders.

OBJECTS AND BRIEF SUMMARY OF THE PRESENT INVENTION

One object of the present invention is to provide a method, and also apparatus, for examining a subject for a particular physiological condition by a technique utilizing acoustic activity of the subject issued at a particular location on the subject's body, and therefore having advantages in one or more of the above respects. Another object of the present invention is to provide a method and apparatus for measuring a large number of physiological conditions of a subject by utilizing, not only the measurements of acoustic activity, but also the measurements of position and/or motion of the subject at the examination site.

According to one aspect of the present invention, there is provided a method of examining a subject for a particular physiological condition by a technique utilizing sounds generated by the subject and modified to be effectively sensed at a predefined distance from the site of sound generation of the subject's body, comprising: locating a first sound sensor at a particular region of the subject's body to produce an output corresponding to the sounds sensed by the first sound sensor; modifying the output of the first sound sensor by a Transfer Function equating the output of the first sound sensor with that of a second sound sensor located at a predetermined distance from the subject's body for calibration of the said first sound sensor; and utilizing the modified output of the first sound sensor in determining the existence of the particular physiological condition; characterized in that said Transfer Function is pre-calculated under controlled laboratory conditions, before used under ambulatory conditions for examining the subject for a particular physiological condition, thereby facilitating examinations under ambulatory conditions while reducing errors caused by ambient factors existing when the method is used under such ambulatory conditions.

In the described preferred embodiments, the Transfer Function is pre-calibrated by: locating the first sound sensor on the particular region of the subject's body; locating the second sound sensor at the predefined distance from the site of sound generation of the subject's body for calibration of the said first sound sensor; simultaneously detecting the sounds sensed by the first and second sensors to produce outputs corresponding thereto; and processing the outputs of the first and second sound sensors to calculate the pre-calculated Transfer Function equating the output of the first sound sensor with that of the second sound sensor.

The first sound sensor located on the particular region of the subject's body may be pre-calibrated to compensate for ambient noise at the particular time it is used for examining the subject for a particular physiological condition, by applying a reference sound generator to the region of the first sound sensor; actuating the reference sound generator simultaneously with the actuation of the first and second sound sensors; processing the two outputs of the first and second sound sensors to determine the difference between the two, which difference represents an Ambient Noise Factor (ANF); and modifying the calculated Transfer Function by the Ambient Noise Factor.

According to another aspect of the present invention, there is provided a method of examining a subject for a particular physiological condition by a technique utilizing sounds generated by the subject and sensed at a predefined distance from the subject, comprising: locating a first sound sensor on a particular region of the subject's body to produce an output corresponding to the sound sensed by the first sound sensor; modifying the output of the first sound sensor by a pre-calculated Ambient Noise Factor equating the output of the first sound sensor with that of a second sound sensor located at a predetermined distance from the subject's body; and utilizing the modified output of the first sound sensor for determining the existence of the particular physiological condition.

According to further features of the invention, the position, and/or motion, of the subject's body at which the first sound sensor is located is also sensed by a position and/or motion sensor located at the particular region of the subject's body, and produces an output which it also utilized to determine the existence of particular physiological condition. By providing the additional position and/or motion sensor on the patient's body at the same location as that of the sound sensor provides the advantages as discussed above making the method particularly useful for sensing snoring or a breathing disorder, sensing blood pressure or other cardiovascular condition of the subject, a joint disorder of the subject involving joint movement related to sound patterns, or a parameter related to the gastrointestinal condition of the subject, as briefly described above.

According to a still further aspect of the invention, there is provided apparatus for examining a subject for a particular physiological condition by a technique utilizing sounds generated by the subject and sensed at a predefined distance from the site of sound generation of the subject's body, comprising: a first sensor constructed to be located at a particular region of the subject's body to produce an output corresponding to the sounds sensed by the first sound sensor; a second sound sensor constructed to be located at a predefined distance from the subject's body, and to produce an output corresponding to the sounds sensed by the second sound sensor; and a processor effective to receive simultaneously the outputs of the two sound sensors, to calculate therefrom a Transfer Function equating the output of the first sound sensor with that of the second sound sensor, to utilize the Transfer Function for modifying the output of first the first sound sensor, and to utilize the modified output of the first sound sensor for producing information useful in determining the existence of the particular physiological condition.

Further features and advantages of the invention will be apparent from the description below.

BRIEF DESCRIPTION OF THE DRAWINGS

The invention is herein described, by way of example only, with reference to the accompanying drawings, wherein.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

FIGS. 1-4 illustrate one preferred embodiment of the invention for examining a subject for a particular physiological condition by monitoring acoustic activity emanating from the subject.

Figure 1:
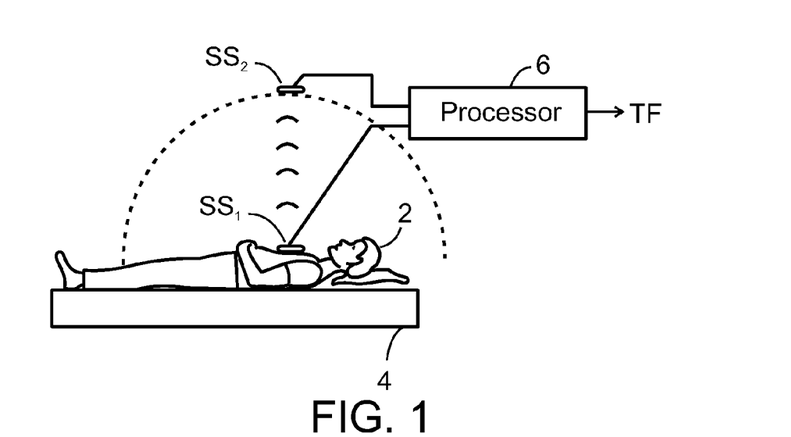
FIG. 1 is a diagrammatic view illustrating the main components of one form of apparatus constructed in accordance with the present invention.

Thus, FIG. 1 illustrates the subject 2 being examined while lying on a bed 4, e.g. while sleeping. As shown in FIG. 1, a sound sensor $SS_1$ is located on a particular region of the subject's body, in this case the chest, to produce an output corresponding to the sounds sensed by sensor $SS_1$. The output of sensor $SS_1$ is fed to a processor 6 for processing as to be described below.

FIG. 1 further illustrates a second sensor $SS_2$ located at a predefined distance from the site of sound generation of the subject's body (as illustrated by the broken arc), e.g. one meter, in accordance with the currently accepted "Gold Standard" technique of analyzing acoustic information.

Processor 6 processes the outputs simultaneously received from the two sensors $SS_1$ and $SS_2$, and produces an output, called a Transfer Function (TF) to be used for equating the output of sound sensor $SS_1$, applied to the subject's body, with the output that would be produced by the second sensor $SS_2$, located at a predefined distance from the site of sound generation of the subject's body, as used in the accepted methods of analyzing acoustical information from the subject for a particular physiological condition.

Figure 2:
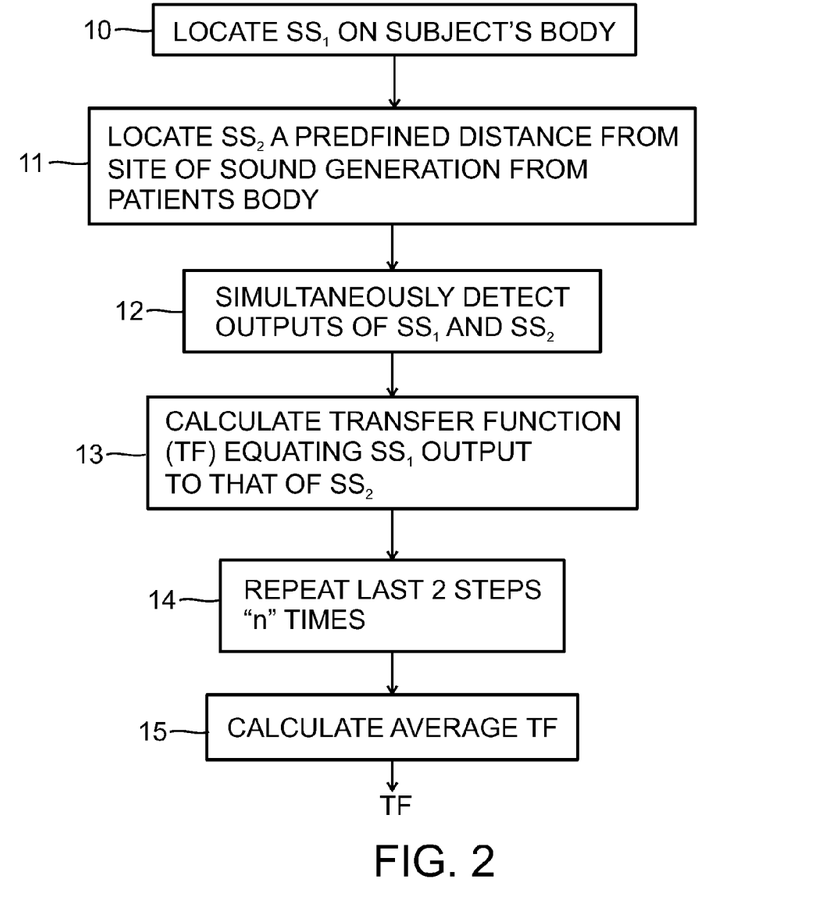
FIG. 2 is a flow chart illustrating the main steps in pre-calibrating the apparatus to determine a Transfer Function equating the output of the sound sensor applied to the subject's body with respect to a sound sensor located at a pre-defined distance from the site of sound generation of the subject's body.

FIG. 2 is a flow chart illustrating the main steps to produce the Transfer Function (TF). Thus, as shown in FIG. 2, the first sensor $SS_1$ is located on the patient's body, whereas the second sensor $SS_2$ is located at a predefined distance (e.g. one meter) from the site of sound generation of the patient's body, as shown by blocks 10 and 11, respectively. The outputs of the two sound sensors $SS_1$ and $SS_2$ are simultaneously detected (block 12), and fed to processor 6, which processes the two outputs to determined the Transfer Function (TF) equating the output of sound sensor $SS_1$ with that of sound sensor $SS_2$ (block 13).

Preferably, the two steps indicated by blocks 12 and 13 are repeated a number of times (block 14), such that the processor 6 calculates the average Transfer Function (TF) for use in equating an output of sound sensor $SS_1$, located on the subject's body, with that which would be detected by sound sensor $SS_2$ located at a predefined distance from the subject's body.

It will be possible that in subsequent examinations of the subject, only the first sound sensor, applied to the subject's body, need be used since its output can be modified by the pre-determined Transfer Function (TF) in order to equate that output to one that would be produced by using a sensor located at a predefined distance (one meter) from the site of sound generation of the subject's body.

In most cases, the first and second sound sensors $SS_1$, $SS_2$ would be sound level meters which measure the sound level in decibels. In some applications, however, it may also be desirable to analyze the outputs of the two sound sensors according to other sensed parameters, e.g., their respective frequency spectra.

In addition, the first sound sensor $SS_1$, during its initial use for determining the Transfer Function (TF), and its later use during the actual examination of the subject, is attached to the subject's body at a particular region. FIG. 1 illustrates this region as being the chest of the subject. However, many measurement sites may be used, e.g., the supra-sternal notch, the submental region, the upper lip, the sides of the neck. Also, the outputs of the two sensors $SS_1$ and $SS_2$ in the pre-calibration stage, or of $SS_1$ alone in the actual examination stage, may be transmitted to processor 6 in a wired or wireless manner.

The sound sensors could be omni directional, as well as directional, microphones. They are preferably attached to the body of the subject at the examination site, e.g., by using an adhesive between the sensor and the body, by taping, or by strapping to the body surface.

Figure 3:
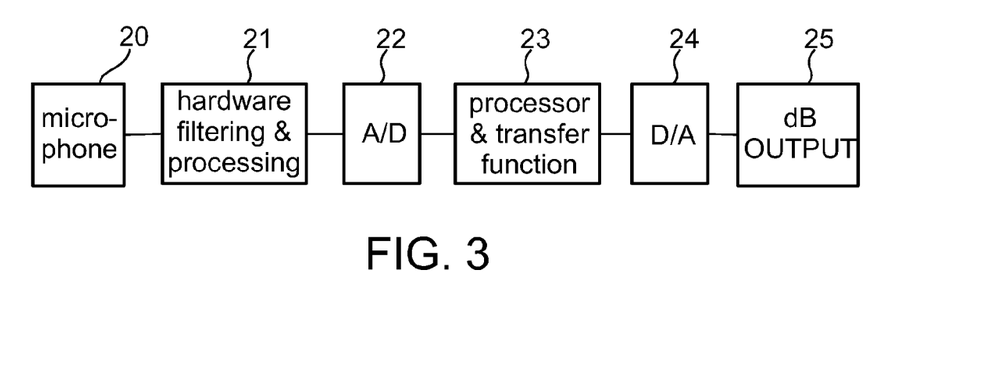
FIG. 3 is a block diagram illustrating the main components of an apparatus constructed in accordance with the present invention for using the Transfer Function (TF) for modifying the output of the sensor applied to the subject's body in order to use the currently accepted acoustic activity techniques to determine the existence of a particular physiological condition.

FIG. 3 is a schematic block diagram illustrating a system for using a single body-applied sensor $SS_1$ after being pre-calibrated to determine in Transfer Function TF, for examining acoustic information emanating from the subject to provide information useful for indicating a particular physiological conditional. Thus, FIG. 3 illustrates the sound sensor in the form of microphone 20 to be applied to the body of the subject and for producing an output to be applied to processor 6 (FIG. 1). Processor 6 performs the hardware filtering and processing functions (block 21) and the analog-to-digital conversion function (block 22). Processor 6 modifies the output from A/D converter 22 by the Transfer Function TF, previously determined in accordance with flow chart 2, to equate the output of microphone 20 with the output that would be obtained by a sound sensor (e.g. microphone $SS_2$, FIG. 1) located at a predefined distance from the site of sound generation of the subject's body, in accordance with current techniques for examining acoustic activity. The output of microphone 20, as modified by the Transfer Function (TF), is then converted to analog information by D/A converter 24, and is displayed as a dB output (block 25).

Figure 4:
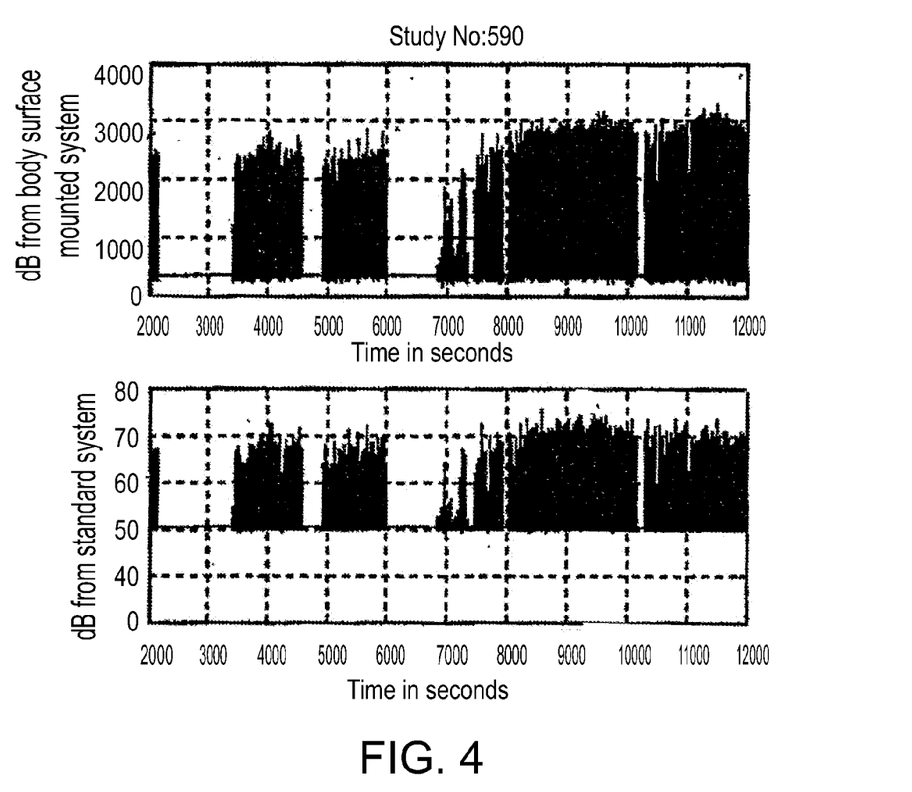
FIG. 4 illustrates the output of a system constructed in accordance with FIG. 3 utilizing a sound sensor located on the subject's body, as compared to one located at a pre-defined distance from the site of sound generation of the subject's body.

FIG. 4 shows the time-course of the acoustic amplitude recorded from the patient's body surface (upper), as compared to the simultaneously recorded acoustic signal recorded by a remote sound recording system (lower). The similarity of the patterns is clearly evident.

The above described method, for converting sound sensed from the body surface to decibel equivalent values using a pre-calibration Transfer Function, was subsequently validated by comparing predicted decibel values to actually recoded decibel values in a group of 19 patients. The resulting comparisons showed that the mean value of the mean difference in each study was 0.7 dB, with a mean standard deviation of 2 dB from the Study standard deviations.

As explained earlier, a main advantage in the ambulatory milieu is gained by placing the sound sensing system on the patient's body surface, rather than at a distance from the patient, since ambient environmental noise cannot be avoided outside the controlled sleep laboratory environment. Placing the sound sensor on the patient thus helps to improve the ability to distinguish between patient derived sounds and irrelevant environmental sounds, since that at a distance from the site of sound generation of the patient's body, the remote sensor is exposed to sounds from all sources. Thus, the body mounted sound detector may still be affected by environmental noise, whether this occurs directly or through external sounds being conducted through or on the body surface, which noise may vary considerably from one measurement environment to the next. This is particularly important when accurate quantitative measurements are required for standardized evaluations, as for example in the measurement of snoring.

A further feature of the present invention is therefore, to include a self-calibration means generating a standardized sound signal between the sensor and the patients body surface. This enables the contribution of external noise to be accurately determined, and thus makes it possible to more accurately measure the endogenous sound activity emanating from the patient. This also makes it possible to use different types of microphones in the system, as required to meet the specific needs of the measurement task. The level of ambient noise can be determined by sensing the sound activity with and without the self-calibration TF signal prior to conducting the patient assessment while the device is attached to the patient. By determining the difference in overall acoustic level with and without the previously determined self-calibration TF signal, the level of ambient noise can be determined and can be used for appropriate correction.

Figure 5:
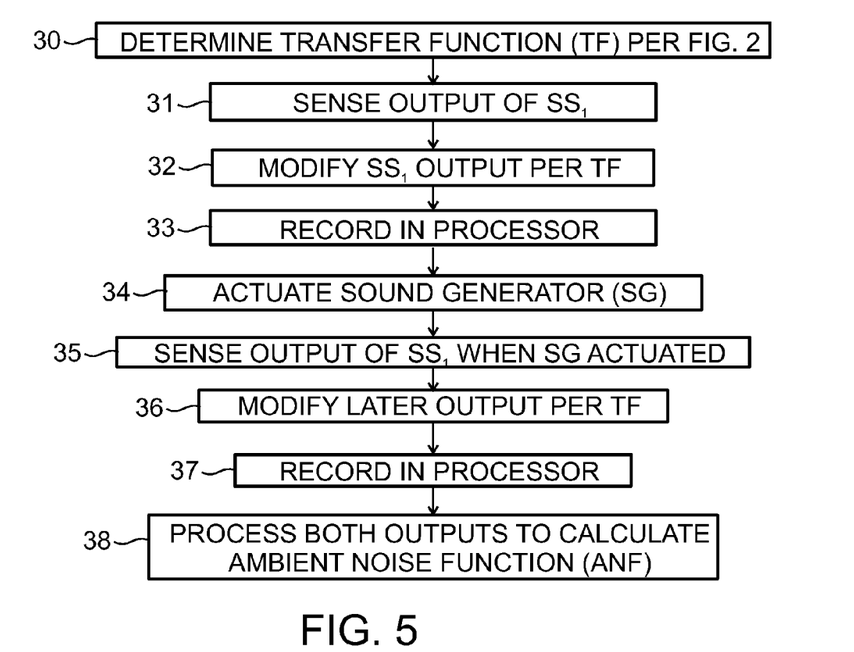
FIG. 5 is a flow chart illustrate a method of determining an Ambient Noise Factor (ANF) in accordance with the present invention for compensating the output of a sound sensor located on the subject's body with respect to the ambient noise conditions existing at the time the examination is made.

FIG. 5 is a flow diagram illustrating a method of self-calibrating the sound sensor ($SS_1$) to be placed on the subject's body in order to determine an Ambient Noise Function (ANF) for the respective sensor at the particular time the subject is to be examined for the physiological condition of interest.

In the flow diagram illustrated in FIG. 5, the Transfer Function (TF) is first determined per the flow diagram of FIG. 2 (block 30). The output of the body-applied sensor $SS_1$ is sensed (block 31), modified by the Transfer Function TF (block 32); and recorded in the processor 6 (block 33).

The sound generator (SG) located at the site of sound sensor $SS_1$ is then actuated (block 34). The output of sensor $SS_1$ is: sensed while the sound generator is actuated (block 35); modified by the Transfer Function TF (block 36), and recorded in the processor (block 37). The processor then processes the two outputs, one produced before the sound generator was actuated, and the other produced after the sound generator was actuated, in order to determine the Ambient Noise Factors (ANF). The ANF may then be used for correcting the body-applied sensor $SS_1$ output during a subsequent examination for determining the existence of the particular physiological condition.

The added sound generator (SG), used for self-calibrating the sound sensor $SS_1$ for determining the ANC, may take the form of an additional element in the system, such as an appropriately designed sound generating piezoelectric sheet (e.g., Mylar), or an off-the-shelf speaker device of appropriately miniature size.

As indicated earlier, a particularly important feature of the present invention is that is also enables the body position or posture, as well as body movements, to be sensed and measurement at the time and site the acoustic information is sensed. Such additional information is very useful in determining various physiological conditions, as described above.

Many sensors are known for sensing body position or posture, and body movement. For example, body position sensors are usually inclination-responsive devices which include an electrically-conductive ball, a quantity of mercury, a bubble, etc., which assume a predetermined position according to its inclination. Motion-responsive devices are usually accelerometer-type devices which produce output signals in accordance with changes in their velocity.

An alternative method is to use a 3D accelerometer unit to measure the angle of the sensor unit with respect to gravity direction, provided that acceleration of the subject during measurement can be neglected with respect to gravity. Also, two 2D accelerometers can be used when there is a common dimension being measured twice to determine the sensors position with respect to gravity, or three mutually orthogonal 1D accelerometers. Accelerometers are preferable since they are not inherently limited to recording just a predetermined small set of orientations, but can in fact provide a continuous range of orientations in the three dimensions, and thus provide the time course of the continuous change of orientation during the test.

Using multi dimension accelerometers as both a body position detector and as a patient movement detector is well known to the art, as disclosed for example in U.S. Pat. Nos. 5,593,431, 6,477,421 and 7,054,687.

The separation of position and motion information is based on appropriate filtering of high and low frequency components of the signals. That is, the low-frequency component of the signal is used for determining the body position, and the high-frequency component is used for determining body motion (to help, for example, in identification of the kind of respiratory pattern). Such a sensor may be used for sensing both patient motion and body position.

Figure 6:
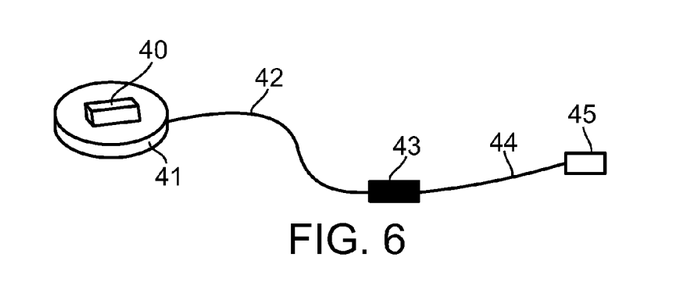
FIG. 6 schematically illustrates a system constructed in accordance with the present invention including a microphone type sound sensor, a position or posture sensor, and a motion sensor, all to be located at the same examination site on the subject's body, wherein the above listed elements are housed within a common housing.

FIG. 6 schematically illustrates one form of apparatus constructed in accordance with the present invention utilizing a posture and motion sensor 40 located on the microphone 41 used as the body-applied sound sensor ($SS_1$, FIG. 1). The relative placement of microphone 41, with respect to posture and motion sensor 40, could be inverted, or these elements could be arranged in a side by side manner. As shown in FIG. 6, the output of microphone 41 is conveyed by cable 42 to processor 43, corresponding to processor 6 in FIG. 1, which processes the information as described above and feeds same via cable 44 to output connector 45.

Figure 7:
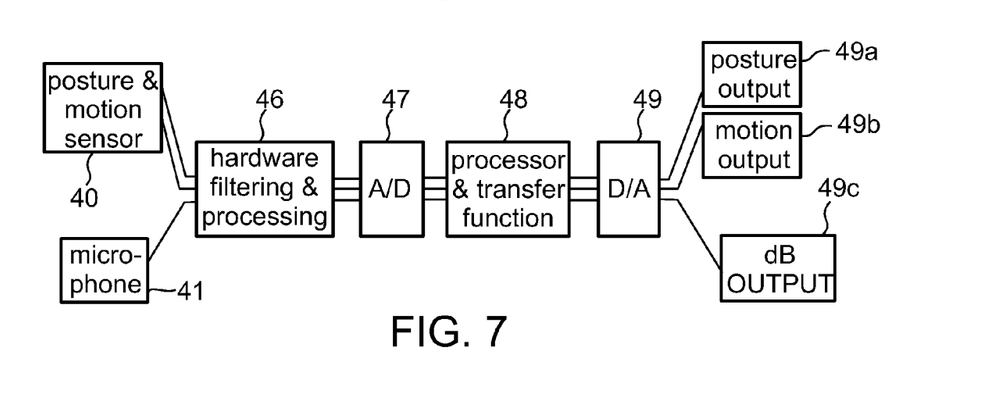
FIG. 7 is a block diagram illustrating the use of the apparatus of FIG. 6 in determining the existence of a particular physiological condition in the subject.

FIG. 7 is a block diagram of the overall apparatus illustrating particularly the functions performed by processor 43 in FIG. 6. Thus, as shown in FIG. 7, processor 43 performs the functions of: filtering and processing the received signals (block 46); converting the processed signals to digital form (block 47); determining the Transfer Function TF (block 48); reconverting the latter signal to analog form (block 49); and then producing the various outputs illustrated in FIG. 7, including a posture output 49a, a motion output 49b, and a dB output 49c.

An important feature of the present invention is that it enables replaying the acoustic, body position, and body movement, information for subsequent analysis and viewing after a study has been conducted.

In the case of the acoustic information, the actual recorded information can be used, together with any means known to the art, to reproduce the sounds recorded during the actual study, or may be represented as a graphical display depicting the sound magnitude and a representation of the frequency content. As previously mentioned, this information can, among other things, provide relevant information to help understand the condition of the air pathway in the respiratory system, and to define the extent and or location of a specific obstruction in the airway of the respiratory system.

Likewise, the position information can be displayed in a visual manner in a multitude of ways. One particularly effective method of displaying the body position information would be to utilize the acquired digital information to drive a visual display showing a mannequin in the body positions corresponding to that of the subject during the study. Body surface movement information can also be visually displayed utilizing a variety of methods, including a graphically display depicting the movement magnitude and a representation of the frequency profile or content.

In all the above, the relevant data, in any combination, can be displayed as a time series, and this will greatly assist in the clinical evaluation of the study. All of the acquired signals may furthermore be represented as outputs in concert with any other data acquired during the study.

Figure 8:
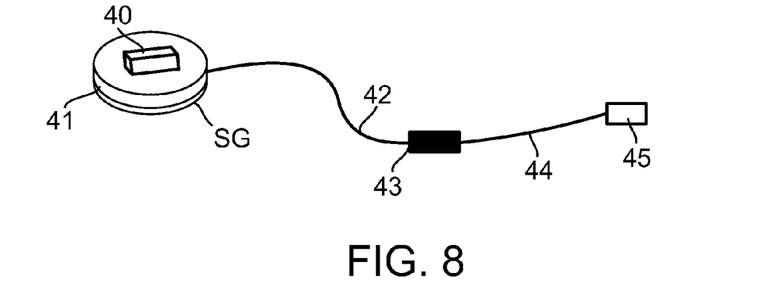
FIG. 8 schematically illustrates a system in accordance with FIG. 8 but modified to enable the system also to be used for calculating an Ambient Noise Factor (ANF) to compensate for noise existing at the time the invention is made.

FIG. 8 schematically illustrates apparatus constructed in accordance with the present invention enabling self-calibration of the apparatus for the Ambient Noise Factor (ANF) as described above particularly with reference to the flow chart of FIG. 5. Thus, such an apparatus is basically constructed as in FIG. 6, and therefore the same reference numerals have been used to identify the parts, except that a sound generator SG has been added to the sensors 40 and 41. As described above, particularly with reference to the flow chart of FIG. 5, the sound generator SG is used in order to self-calibrate the sensors 40, 41 for ambient or transient noise by determining the ANF (Ambient Noise Factor) for the particular sensors used, and for the particular ambient conditions at the time the examination is to be made.

Figure 9:
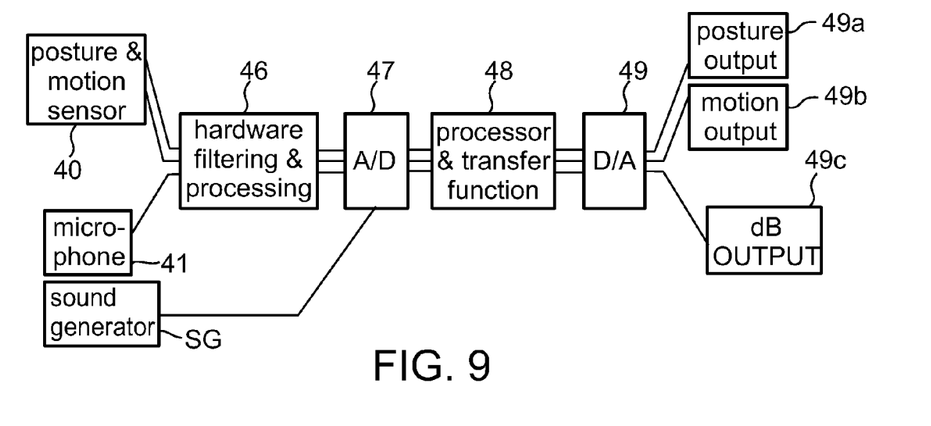
FIG. 9 is a block diagram illustrating the use of the apparatus of FIG. 8.

FIG. 9 is a block diagram, corresponding to that of FIG. 7, but also including the sound generator SG. The block diagram is otherwise the same as in FIG. 7, and therefore the same reference numerals have been used to identify corresponding parts, except for the addition of the sound generator SG.

Figure 10:
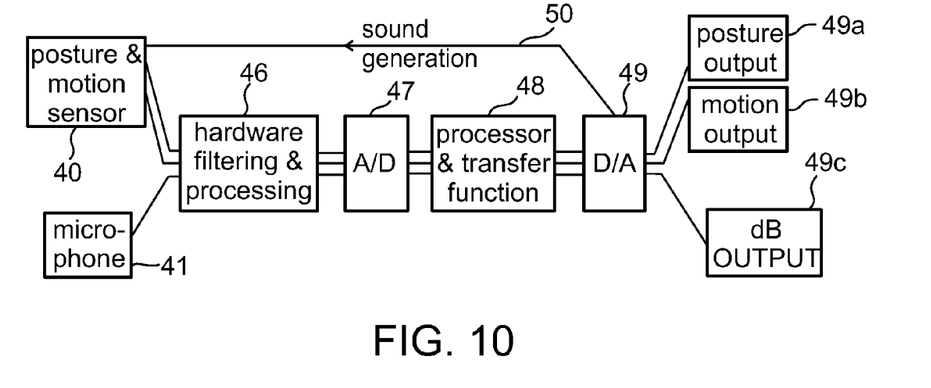
FIG. 10 is a block diagram illustrating the system of FIGS. 8 and 9 but wherein the sound activity provided by the calibration means is derived from the body movement sensor.

FIG. 10 illustrates an alternative system that may be used instead of FIG. 9, wherein the sound activity provided by the calibration means is derived from the accelerometer device used for body position and body movement determination.

Thus, in the system illustrated in FIG. 10, the sound generator SG of FIG. 9 is omitted, and instead, a feedback line 50 is applied from the digital/analog converter 49 for feeding the analog of the output from the processor back to the posture and motion sensor 40.

The present invention may be used in combination with any known medical device in which the addition of all or some of the measured signals may be of value. The invention may itself also be used as an independent measurement system by being coupled to an appropriate data collection system for utilizing the available data. Multiple devices may be applied at the same time to different body sites to further enhance the recording of useful information. Examples of such beneficial combination may include the comparison of homologous joints to differentially identify joint problems, the recording of respiratory sound information at different sites to help identify the location of the source of the sound, heart sounds at different locations to help identify the nature of abnormal sounds, etc.

Therefore, while the invention has been described with respect to several preferred embodiments, it will be appreciated that these are set forth merely for purposes of example, and that many other variations, modifications and applications of the invention may be made.

The invention claimed is:

1. A method of examining a subject for a particular physiological condition using at least one estimated parameter of sound produced by a site of sound generation of a subject's body and determined as for a location away from the subject's body at a predefined distance from said site, thereby emulating output of a second hardware sound sensor, the method comprising:
   placing a first hardware sound sensor on a particular region of the subject's body;
   sensing sounds with the first hardware sound sensor so as to avoid an environmental noise sensed when the second hardware sound sensor is located at the location away from the subject's body which is at the predefined distance from the site of sound generation of the subjects body:
   producing a sensor output corresponding to the sounds sensed by said first hardware sound sensor;
   modifying using a hardware signal processor the output of said first hardware sound sensor by a pre-calculated Transfer Function equating the output of the first hardware sound sensor with an emulated output, the output emulated being of the second hardware sound sensor, when the second hardware sound sensor is located at said predefined distance from the site of sound generation of the subject's body and configured to sense sound generated at said site;

said equating comprising converting said output of said first hardware sound sensor to the decibel equivalent values of sound sensed at said predefined distance from the site of sound generation; and determining an existence of said particular physiological condition based on the modified output of said first hardware sound sensor.

2. The method according to claim 1, wherein said transfer function is pre-calculated by:
placing said first sound sensor on said particular region of the subject's body;
placing said second sound sensor at said predefined distance from the site of sound generation of the subject's body for calibration of the first sound sensor;
simultaneously detecting the sounds sensed by said first and second sound sensors to produce outputs corresponding thereto; and
processing said outputs of the first and second sound sensors to calculate said pre-calculated transfer function equating the output of said first sound sensor with that of said second sound sensor.

3. The method according to claim 1, wherein said first and second sound sensors are sound level meters which measure the sound level in decibels, and wherein said first sound sensor is attached to the subject's body at said particular region.

4. The method according to claim 1, wherein said first sound sensor is pre-calibrated to compensate for ambient noise at the particular time the first sound sensor is used for examining the subject for a particular physiological condition, by:
applying a reference sound generator to the region of said first sound sensor;
locating the second sound sensor at said predefined distance from the site of sound generation of the subject's body and configuring the second sound sensor to sense sound generated at said site;
actuating said reference sound generator simultaneously with the actuation of said first and second sound sensors;
processing the outputs of each of said first and second sound sensors to determine the difference between the two, which difference represents an Ambient Noise Factor (ANF); and
modifying said calculated transfer function by said Ambient Noise Factor.

5. The method according to claim 1, wherein the position of the subject's body at which said first sound sensor is located is sensed by:
placing a position sensor at said particular region of the subject's body; and
producing an output from the position sensor which is also utilized in determining the existence of said particular physiological condition.

6. The method according to claim 5, wherein movement of the subject's body is sensed by:
placing a motion sensor at said particular region of the subject's body, and producing an output from the motion sensor which is also utilized in determining the existence of said particular physiological condition.

7. The method according to claim 1, wherein said particular physiological condition is snoring or a breathing disorder.

8. The method according to claim 1, wherein said particular physiological condition is blood pressure, heart valve closure condition, or other cardiovascular condition of the subject.

9. The method according to claim 1, wherein said particular physiological condition is a joint disorder of the subject detected by also measuring a joint movement in space based on sound patterns related to the joint movement and sensed by said first sound sensor.

10. The method according to claim 1, wherein said particular physiological condition is related to the gastrointestinal system of the subject.

11. The method according to claim 6, further including replaying the sensed sound output, position sensor output, and motion sensor output for subsequent analysis and viewing after a study has been conducted.

12. The method according to claim 1, wherein said first and second sound sensors are microphones.

13. The method according to claim 1, wherein said first hardware sound sensor is constructed to be placed at said particular region of the subject's body so as to reduce acoustic crosstalk due to the environmental noise when said second hardware sound sensor is placed at a predefined distance.

14. Apparatus for examining a subject for a particular physiological condition by using at least one estimated parameter of sound produced by a site of sound generation of a subject's body and determined as for a location away from the subject's body at a predefined distance from said site, comprising:
a first hardware sound sensor constructed to be placed at a particular region of the subjects body to produce an output corresponding to the sounds sensed by said first hardware sound sensor so as to avoid an environmental noise sensed when a second hardware sound sensor is placed at the location away from the subject's body at the predefined distance from the site of sound generation of the subjects body, said second hardware sound sensor is used for calibration of the first hardware sound sensor, and to produce an output corresponding to the sounds sensed by said second hardware sound sensor and configured to sense sound generated at said site; and
a hardware processor effective to receive simultaneously the outputs of said first and second hardware sound sensors, to calculate from the outputs of the first and second hardware sound sensor a transfer function equating the output of said first hardware sound sensor with an output of said second hardware sound sensor, said equating comprising converting said output of said first hardware sound sensor to decibel equivalent values of sound sensed at said predefined distance from the site of sound generation, and comprising a hardware signal processor effective to utilize said transfer function for so-modifying the output of said first hardware sound sensor, and
wherein the processor is effective to determine an existence of said particular physiological condition based on said modified output of said first hardware sound sensor.

15. The apparatus according to claim 14, wherein said apparatus also includes:
a position sensor constructed so as also to be placed at said particular region of the subject's body; and
said processor is also effective to utilize the output of said position sensor for producing information useful in determining said particular physiological condition.

16. The apparatus according to claim 14, wherein said apparatus also includes a reference sound generator also to be placed at said particular region of the subject's body, to generate reference sounds for use in determining an Ambient Noise Factor (ANF) to be used for pre-calibrating the apparatus for the ambient noise at the time the output of said first sound sensor is used for producing information useful in determining the existence of said particular physiological condition.

17. The apparatus according to claim 16, wherein said first sound sensor, a position sensor, and said reference sound generator and a motion sensor, are housed within a common housing.

18. The apparatus according to claim 15, wherein said particular physiological condition is at least one of:
- a snoring or a breathing disorder,
- a measured blood pressure,
- a heart valve closure condition, or other cardiovascular condition of the subject,
- a joint disorder of the subject detected by measuring a joint movement in space based on sound patterns related to the joint movement and sensed by said first sound sensor, and
- a condition related to the gastrointestinal system of the subject.

19. The apparatus according to claim 16, wherein said motion sensor comprises said reference sound generator.

20. The apparatus according to claim 16, wherein said position sensor comprises said reference sound generator.

21. The apparatus according to claim 14, wherein said processor is effective to modify of the output of said first sound sensor by reduction in said decibel equivalent value according to a gain reduction.

* * * * *